(12) United States Patent
Lee et al.

(10) Patent No.: US 12,274,472 B2
(45) Date of Patent: Apr. 15, 2025

(54) TROCAR

(71) Applicant: LIVSMED INC., Seongnam-si (KR)

(72) Inventors: Jung Joo Lee, Seongnam-si (KR);
Heejin Kim, Seongnam-si (KR);
Dongkyu Jang, Seongnam-si (KR);
Jinho Kwon, Seongnam-si (KR);
Jaeyeong Lee, Seongnam-si (KR)

(73) Assignee: LIVSMED INC., Seongnam-si (KR)

( * ) Notice: Subject to any disclaimer, the term of this patent is extended or adjusted under 35 U.S.C. 154(b) by 0 days.

(21) Appl. No.: 18/597,895

(22) Filed: Mar. 6, 2024

(65) Prior Publication Data
US 2024/0206911 A1  Jun. 27, 2024

Related U.S. Application Data

(60) Division of application No. 17/487,890, filed on Sep. 28, 2021, now Pat. No. 11,950,806, which is a continuation of application No. PCT/KR2020/017256, filed on Nov. 30, 2020.

(30) Foreign Application Priority Data

Sep. 28, 2020 (KR) ........................ 10-2020-0126002

(51) Int. Cl.
*A61B 17/34* (2006.01)
(52) U.S. Cl.
CPC ...... *A61B 17/3423* (2013.01); *A61B 17/3498* (2013.01); *A61B 2017/3466* (2013.01)

(58) Field of Classification Search
CPC ............ A61B 17/3498; A61B 17/3462; A61B 2017/3445; A61B 17/3423
See application file for complete search history.

(56) References Cited

U.S. PATENT DOCUMENTS

| 4,949,717 A | 8/1990 | Shaw |
| 2008/0255519 A1 | 10/2008 | Piskun et al. |
| 2009/0012521 A1* | 1/2009 | Axelson, Jr. .......... A61F 2/0063 |
| | | 606/53 |

(Continued)

FOREIGN PATENT DOCUMENTS

| KR | 10-1151310 B1 | 6/2012 |
| KR | 10-2013-0043875 A | 5/2013 |

(Continued)

*Primary Examiner* — Brigid K Byrd
(74) *Attorney, Agent, or Firm* — Bridgeway IP Law Group, PLLC; Sang Ho Lee; Hyun Woo Shin

(57) ABSTRACT

Provided is a surgical method using a surgical instrument including an end tool having one or more joints and a trocar. The surgical method includes coupling an obturator with a main body of the trocar, inserting the trocar into a body of a patient, separating the obturator from the main body, coupling an end tool mounting member with the main body, and inserting the surgical instrument into the body of the patient through the trocar. In a state in which the end tool of the surgical instrument is mounted on the end tool mounting member, the end tool is rotated in the direction by using a contact point between the end tool and the end tool mounting member as a pivot point, the end tool and a shaft of the surgical instrument are substantially parallel to each other, and the surgical instrument is inserted into the body of the patient.

14 Claims, 9 Drawing Sheets

(56) References Cited

U.S. PATENT DOCUMENTS

| | | |
|---|---|---|
| 2010/0081995 A1 | 4/2010 | Widenhouse et al. |
| 2010/0191166 A1 | 7/2010 | Phillips et al. |
| 2010/0298839 A1 | 11/2010 | Castro |
| 2015/0141964 A1 | 5/2015 | Macmillan et al. |
| 2016/0045220 A1 | 2/2016 | Wachli et al. |
| 2019/0099186 A1* | 4/2019 | Piskun ................... A61B 1/018 |
| 2019/0183527 A1* | 6/2019 | Cartmill ............. A61B 17/3468 |

FOREIGN PATENT DOCUMENTS

| | | |
|---|---|---|
| KR | 10-2014-0097814 A | 8/2014 |
| KR | 10-2015-0105756 A | 9/2015 |
| KR | 10-2017-0043592 A | 4/2017 |

\* cited by examiner

TROCAR

CROSS-REFERENCE TO RELATED APPLICATIONS

The present application is a divisional application of U.S. application Ser. No. 17/487,890 filed on Sep. 28, 2021, which is a continuation application of international application No. PCT/KR2020/017256 filed on Nov. 30, 2020, and claims priority to Korean patent application No. 10-2020-0126002 filed on Sep. 28, 2020, the entire disclosures of which are herein incorporated by reference.

TECHNICAL FIELD

The present disclosure relates to a trocar, and more specifically to a trocar provided with an end tool mounting member capable of placing an end tool of a surgical instrument thereon, thereby facilitating the insertion of the surgical instrument having multiple joints into the trocar.

BACKGROUND ART

Medically, surgery refers to the treatment of a disease by cutting, slitting or manipulating skin, mucous membrane, or other tissues by using medical devices. In particular, laparotomy, which cuts and opens the skin of a surgical site and treats, molds, or removes an organ or the like therein, causes, for example, bleeding, side effects, pain of a patient, scars, and the like. Accordingly, surgery using a robot or a surgical operation in which a certain hole is formed in the skin and only a medical device, for example, a laparoscope, a surgical instrument, a microsurgical microscope, or the like, is inserted, has recently been spotlighted as an alternative manner.

A surgical instrument is a tool with which a surgeon performs an operation by directly manipulating, with his or her hands and by using an operating unit, an end tool provided to an end of a shaft passing through a hole perforated in the skin, or manipulating the end tool by using a robot arm. The end tool included in the surgical instrument performs a rotating operation, a gripping operation, a cutting operation, and the like through a certain structure.

According to the laparoscopic surgery, a tube is made through the abdomen of a patient using a surgical instrument called a trocar, and a surgical instrument, a laparoscopic instrument and the like are introduced into the surgical site of the abdominal cavity through the trocar, thereby allowing the surgical operation to perform while the surgical site of the abdominal cavity is observed.

The above-described background technology is technical information that the inventor has possessed for the derivation of the present disclosure or acquired in the derivation process of the present disclosure, and shall not be called a publicly known technology which is published to the general public before the present disclosure is filed.

DESCRIPTION OF EMBODIMENTS

Technical Problem

The present disclosure is to provide a trocar, wherein an end tool mounting member is provided to place an end tool of a surgical instrument thereon, thereby facilitating the insertion of the surgical instrument having multiple joints into the trocar.

Technical Solution to Problem

An embodiment of the present disclosure provides a trocar including: a main body having a hollow portion formed therein to allow a surgical instrument to be inserted therethrough; a cannula coupled to an end of the main body and having a hollow portion formed therein to allow the surgical instrument to be inserted therethrough; an end tool mounting member which is detachably formed on the other end of the main body and has an inclined portion formed on an inner circumferential surface thereof to allow the end tool of the surgical instrument to be placed thereon; and an obturator detachably formed at the other end of the main body and performing a function of opening and closing the other end of the main body.

Other aspects, features, and advantages other than those described above will become clear from the following drawings, claims, and detailed description of the disclosure.

Advantageous Effects of Disclosure

Due to the facilitation of the insertion into a trocar of a surgical instrument having multiple joints according to the present disclosure, the convenience of an operator may be enhanced, and the accuracy, reliability, and promptness of the surgical operation may be improved.

BEST MODE

Figure 1:
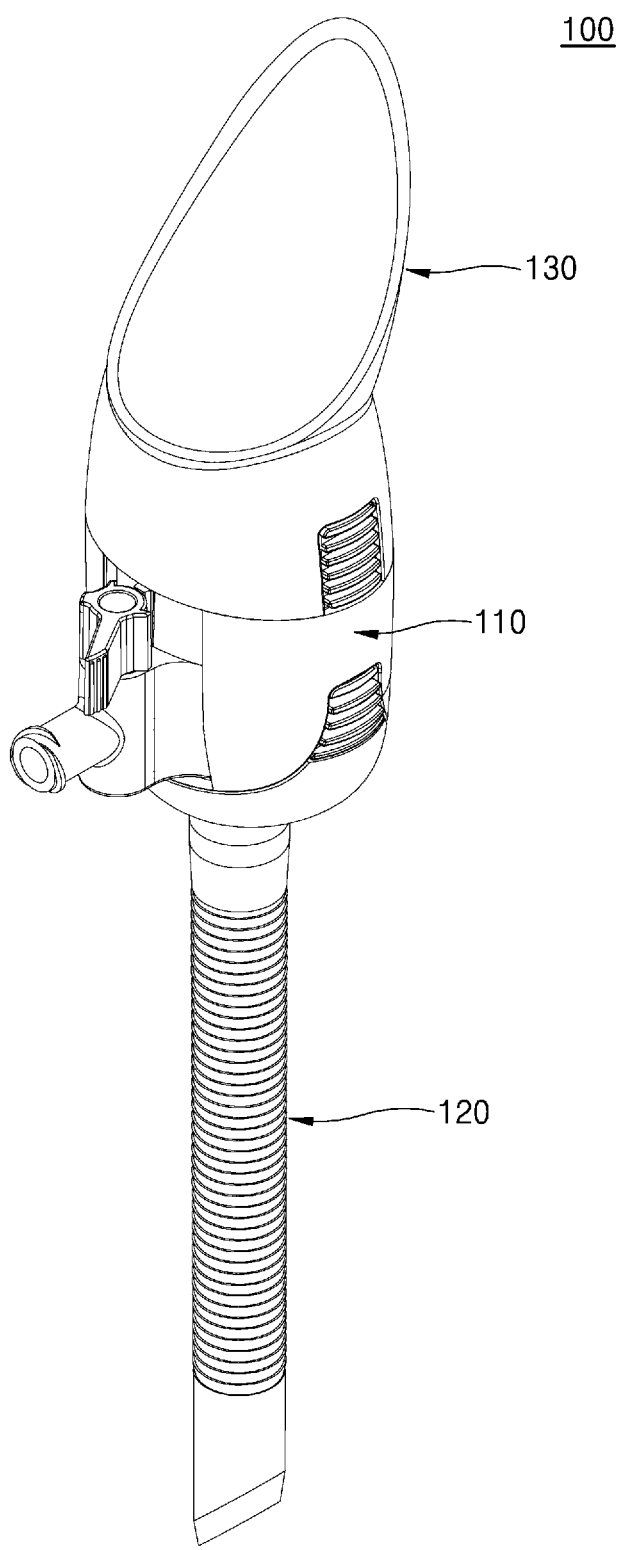
FIG. 1 shows an assembled perspective view illustrating a trocar according to an embodiment of the present disclosure.

The present disclosure may be subjected to various modifications and may have various embodiments. Accordingly, specific embodiments will be illustrated in the drawings and described in detail. However, this is not intended to limit the present disclosure to specific embodiments, and it should be understood that the present disclosure includes all modifications, equivalents, and substitutes that are included within the concept and technical scope of the present disclosure. In describing the present disclosure, when it is determined that a detailed description of a related known technology may make the gist of the present disclosure unclear, the detailed description thereof will be omitted.

Terms "first" and "second" may be used to describe various elements, but the elements should not be limited by the terms. The terms are used only to distinguish one element from another element.

The terminology used herein is intended to describe particular embodiments only and not to limit the present disclosure. The singular expression includes the plural expression unless the context clearly dictates otherwise. The terms "include" or "have" used herein are intended to designate that a feature, a number, a step, an operation, a component, a part, or a combination thereof described in the specification exists, and do not preclude the possibility of the presence or addition of one or more other features, numbers, steps, operations, components, parts, or combinations thereof.

Hereinafter, embodiments of the present disclosure will be described in detail with reference to the accompanying drawings, and in the description with reference to the accompanying drawings, the same or corresponding elements will be denoted by the same reference numerals, and a repeated description thereof will be omitted.

Further, in describing various embodiments of the present disclosure, it should be understood that each embodiment is not to be interpreted or practiced independently, and that the technical concepts described in each embodiment may be interpreted or practiced in combination with other embodiments described separately.

Figure 2:
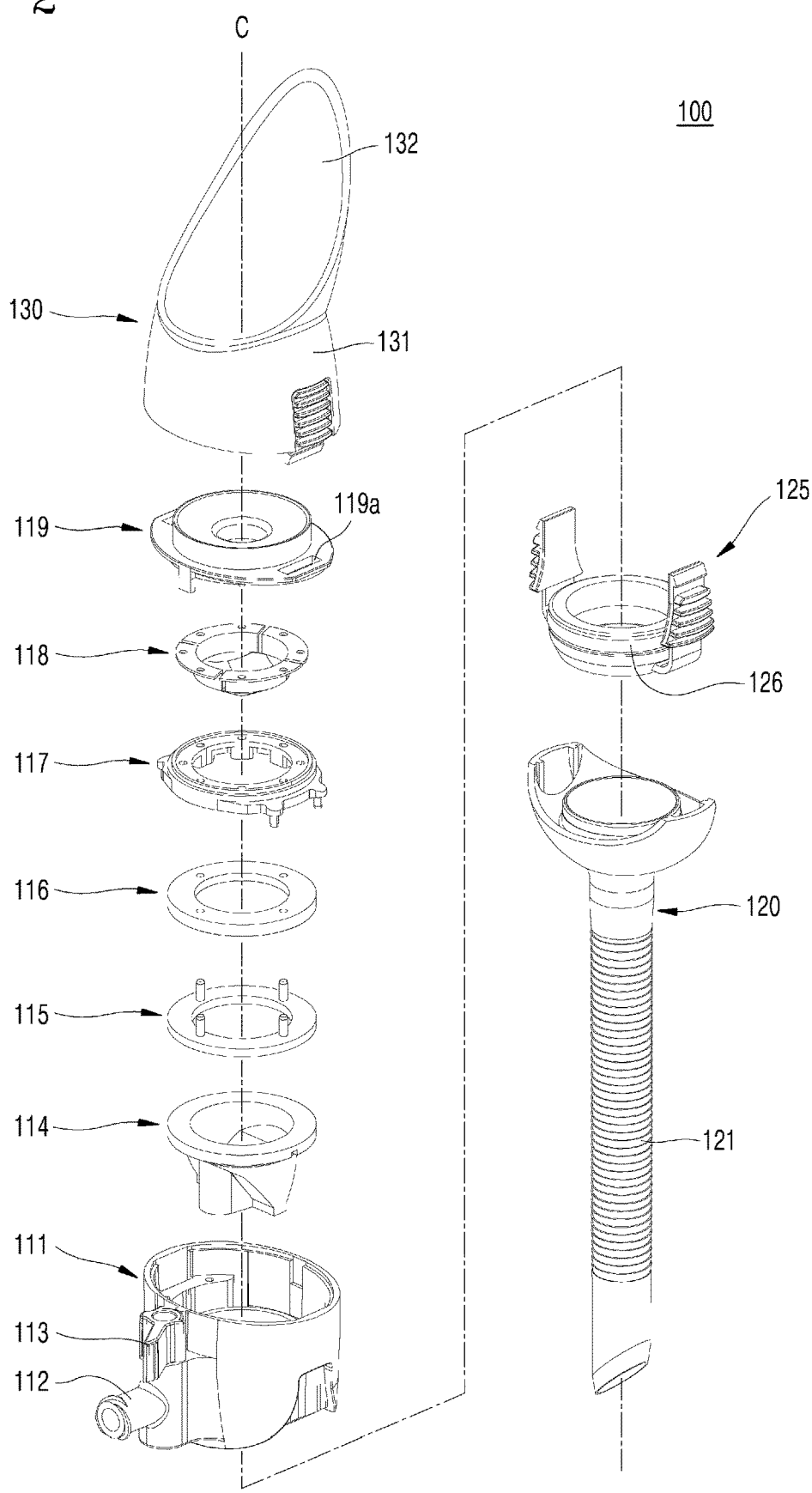
FIG. 2 shows an exploded perspective view of the trocar of FIG. 1.
Figure 3:
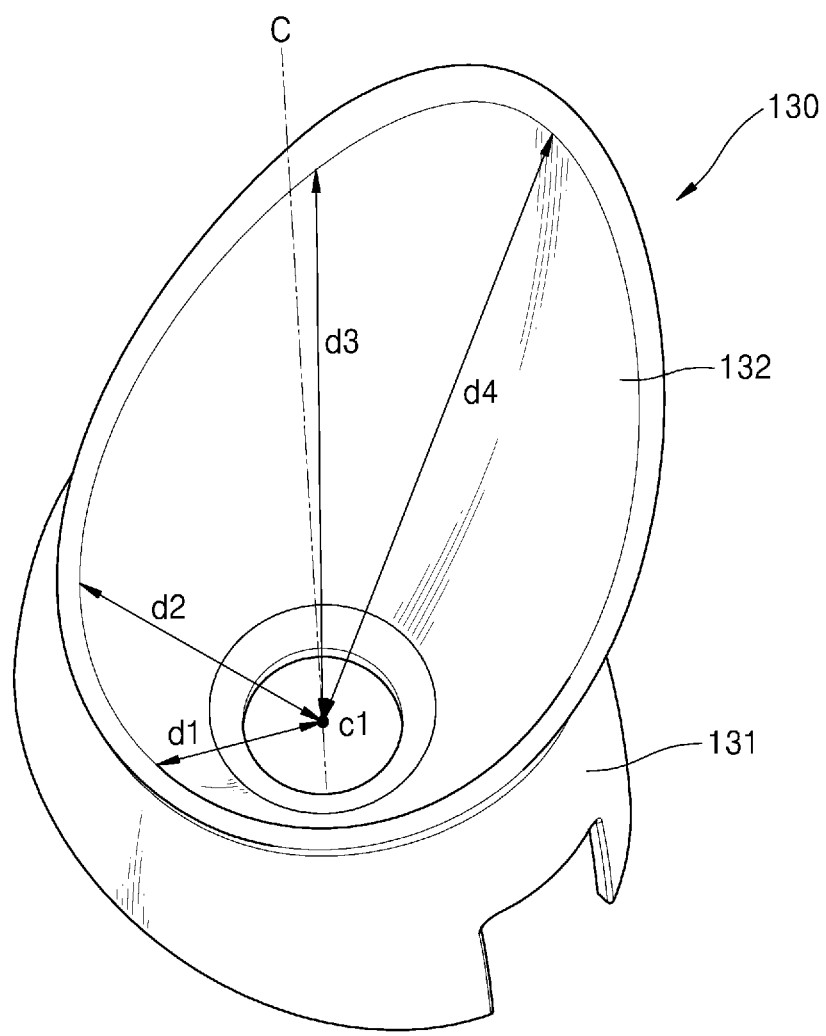
FIG. 3 shows a perspective view of an end tool mounting member of the trocar of FIG. 1.
Figure 4:
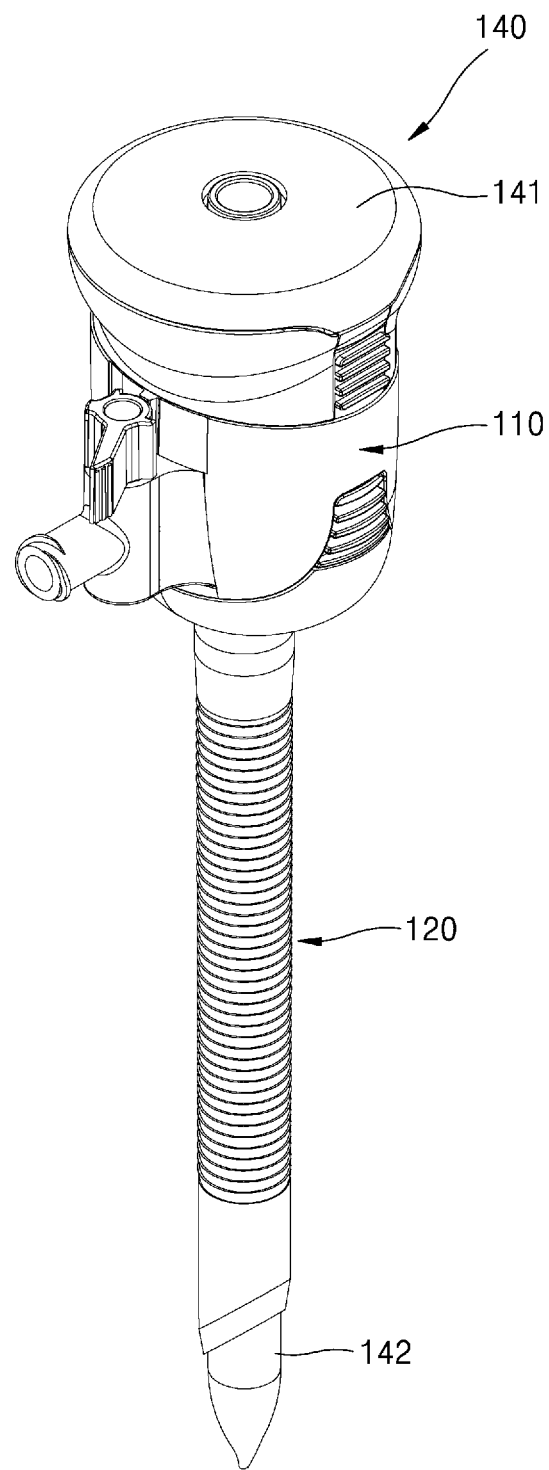
FIG. 4 shows a perspective view illustrating an example of the trocar of FIG. 1 with an obturator coupled thereto instead of an end tool mounting member.
Figure 5:
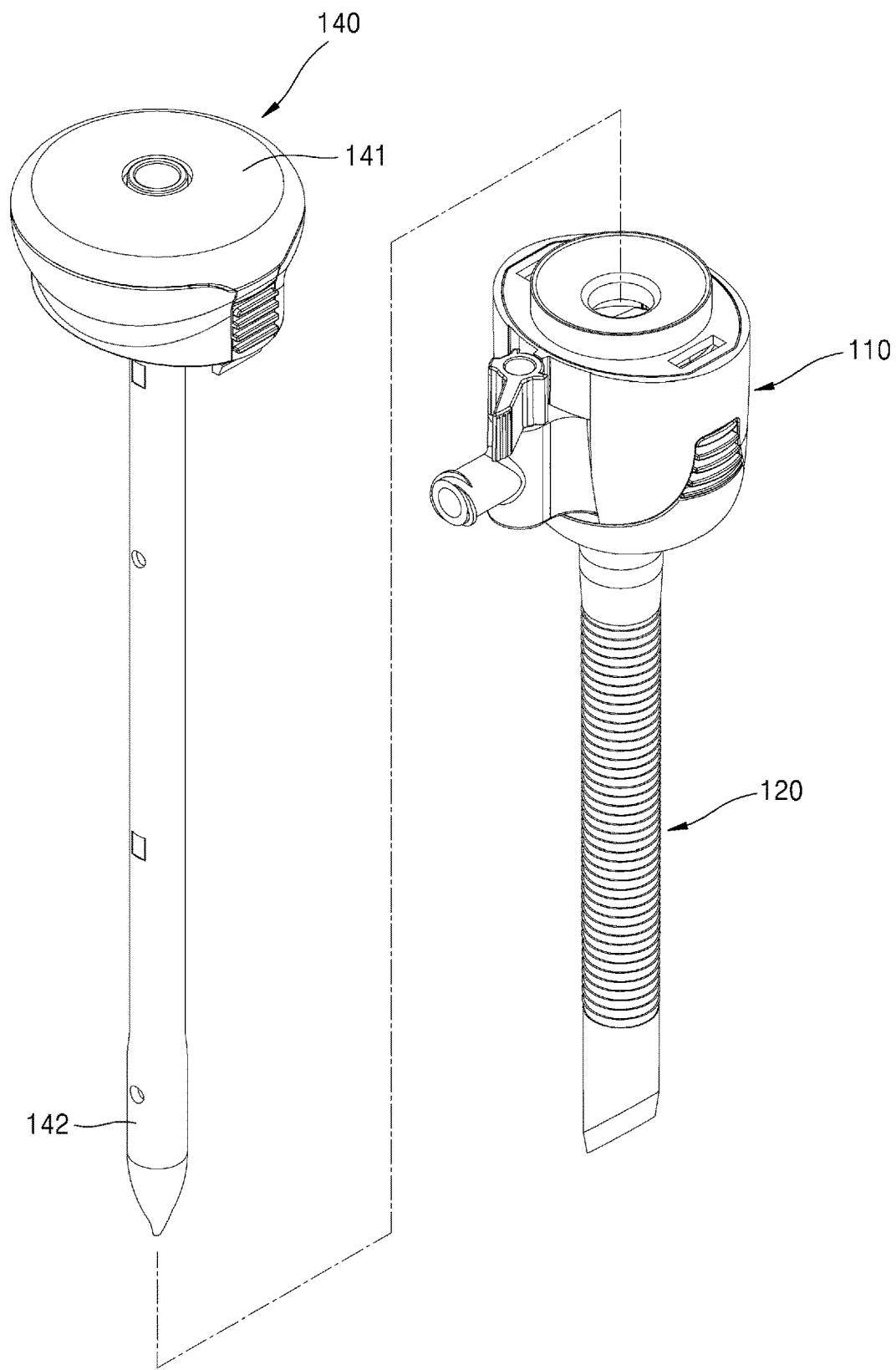
FIG. 5 shows an exploded perspective view of the trocar of FIG. 4.

FIG. 1 shows an assembled perspective view illustrating a trocar 100 according to an embodiment of the present disclosure, and FIG. 2 shows an exploded perspective view of the trocar 100 of FIG. 1. FIG. 3 shows a perspective view of an end tool mounting member 130 of the trocar 100 of FIG. 1. FIG. 4 shows a perspective view illustrating an example of the trocar 100 of FIG. 1 with an obturator 140 coupled thereto instead of an end tool mounting member. FIG. 5 shows an exploded perspective view of a trocar of FIG. 4.

Referring to FIGS. 1 to 5, the trocar 100 according to an embodiment of the present disclosure includes a main body 110, a cannula 120, the end tool mounting member 130, and the obturator 140.

Conventional surgical instruments for passive laparoscopic surgery generally include straight instruments having no joints at an end tool. Since such straight instruments have no joints, the end tool may not be bent. Accordingly, it is not difficult to insert the straight instrument into the trocar.

However, in the case of the conventional surgical instrument, since the end tool is not bent, it is not easy to access the surgical site and perform various surgical operations.

In order to address these problems, the applicant of the present application has developed an instrument for multi-joint multi-degree of freedom laparoscopic surgery capable of performing pitch, yaw, and actuation motions.

Figure 6:
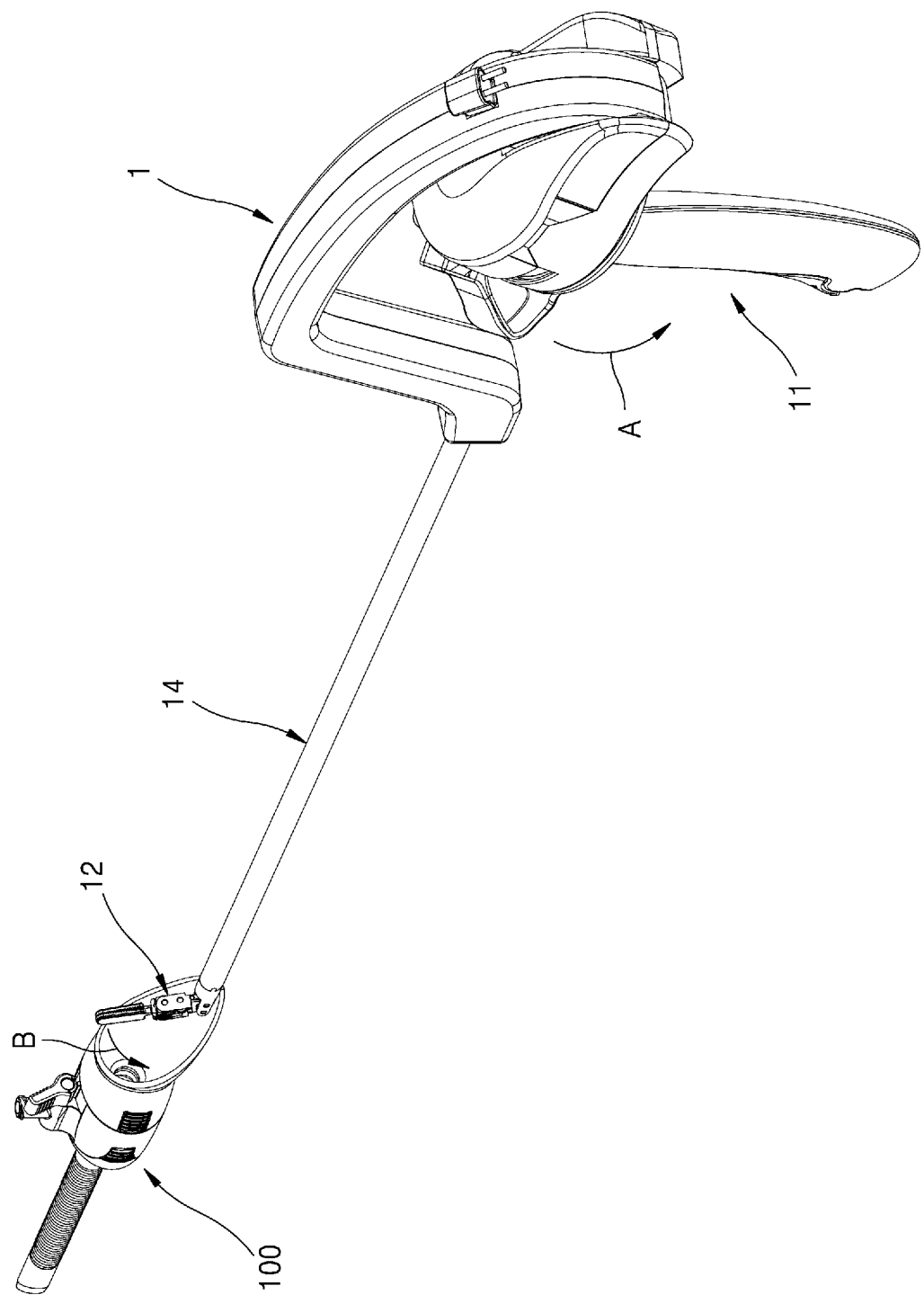
FIG. 6 and FIG. 7 show views illustrating an aspect of the usage of the trocar of FIG. 1.

However, during actual surgery, a surgeon often performs surgery with surgical instruments held in both hands one by one, and when the multi-joint, multi-degree of freedom laparoscopic surgical instrument is held in one hand, an end tool 12 is approximately perpendicular to the shaft 14 by the weight thereof as shown in FIG. 6.

In this state, however, since a surgical instrument 1 may not be inserted into the trocar 100, an assistant needs to hold the surgical instrument 1 and adjust the end tool 12 to be parallel with the shaft 14.

In order to address this problem, the trocar 100 according to an embodiment of the present disclosure includes the end tool mounting member 130. Due to the providing of a structure that allows the end tool (see 12 of FIG. 6) of the surgical instrument 1 to be placed thereon, the performer may easily make the end tool (see 12 of FIG. 6) and the shaft (see 14 of FIG. 6) to be parallel to each other, thereby easily inserting the end tool (see 12 of FIG. 6) into the trocar 100.

Hereinafter, the present embodiment will be described in more detail.

Referring to FIGS. 1 to 5, the main body 110 may be a structure having a hollow portion formed therein to allow the surgical instrument 1 to be inserted therethrough. In an embodiment, various components for executing functions of the trocar 100 are disposed in the main body 110.

In detail, the main body 110 may include a main body case 111, a gas insertion pipe 112, a gas valve 113, a check valve 114, a sealing pad 116, a sealing pad fixing member 115, an auxiliary pad 118, an auxiliary pad fixing member 117, and a main body cap 119.

The main body case 111 may be formed in a hollow cylindrical shape to accommodate therein components of the main body 110 to be described below.

The gas insertion pipe 112 extends in one direction from one side surface of the main body case 111. Carbon dioxide may be injected into the patient's body by supplying the carbon dioxide through the gas insertion pipe 112. The injected carbon dioxide may inflate the abdominal cavity of the patient to secure a space for performing laparoscopic surgery. The gas insertion pipe 112 may include, for example, plastic, or may include a soft material that is elastically deformed, so that the gas insertion pipe 112 may be elastically bent.

The gas valve 113 may be formed on the gas insertion pipe 112 to control the opening/closing of the gas insertion pipe 112.

The check valve 114 may prevent the gas (carbon dioxide) inserted into the body through the gas insertion pipe 112 from being discharged to the outside of the trocar 100. The check valve 114 may be fixedly coupled inside the main body case 111, and when the surgical instrument 1 is inserted into the body, the check valve 114 is opened, and when the surgical instrument 1 is separated from the body, the check valve 114 is closed. By doing so, the check valve 114 may prevent the gas injected into the body from leaking to the outside.

To this end, the check valve 114 may include, for example, silicon having a certain level of elastic force. Meanwhile, a cutting line (not shown) may be formed at a central portion of the check valve 114. In an embodiment, a reinforcing member for preventing the check valve 114 from being overturned may be further formed on the inclined surface of the check valve 114.

In a state in which no external force is applied, the cutting lines (not shown) of the check valve 114 are maintained as being in close contact with or close to each other, so that the not-opened state is maintained, and when the surgical instrument 1 is inserted (inserted in a downward direction) and presses the check valve 114, the check valve 114 is open at the cutting lines and the surgical instrument 1 passes through the check valve 114.

The sealing pad 116 may seal the gas so that the gas injected into the body does not leak to the outside when the check valve 114 is opened due to the insertion of the surgical instrument 1. The sealing pad 116 may be formed in a conical shape, and a through-hole through which the surgical instrument 1 may pass, may be formed in a vertex area thereof. In this case, the diameter of the through-hole may be equal to or slightly smaller than the diameter of the shaft 14 of the surgical instrument 1, so that the surgical instrument 1 may be formed to be closely coupled to the through-hole of the sealing pad 116. As described above, due to the sealing pad 116 formed to be in close contact with the outer circumferential surface of the shaft 14 of the surgical instrument 1, even during the check valve 114 is opened, the gas injected into the patient's body may not leak to the outside. Like the check valve 114, the sealing pad 116 may include a silicon material.

That is, the check valve 114 may be in charge of sealing the trocar 100 in the case where the surgical instrument 1 is not inserted into the trocar 100, and the sealing pad 116 may be in charge of sealing the trocar 100 in the case where the surgical instrument 1 is inserted into the trocar 100.

The sealing pad fixing member 115 may be disposed on the check valve 114 and may be formed such that the sealing pad 116 is coupled thereto, thereby fixing the position of the sealing pad 116. For example, a plurality of holes may be formed in the sealing pad 116, and a plurality of protrusions may be formed in the sealing pad fixing member 115, and the position of the sealing pad 116 may be fixed by inserting the protrusions into the holes.

The auxiliary pad 118 may prevent the sealing pad 116 from being turned upside down when the surgical instrument 1 is inserted into or withdrawn from the trocar 100.

The auxiliary pad fixing member 117 may be disposed above the sealing pad 116, and may be formed such that the auxiliary pad 118 is coupled thereto, thereby fixing the position of the auxiliary pad 118. In this case, the auxiliary pad fixing member 117 may be fixedly coupled to the inside of the main body case 111, so that the positions of the auxiliary pad fixing member 117 and the auxiliary pad 118 coupled thereto may be fixed.

The main body cap 119 may be coupled to an upper portion of the main body case 111, and may couple these members disposed inside the main body case 111 to one another and seal the same. Herein, the main body cap 119 may be provided with a coupling portion to which the end tool mounting member 130 and/or the obturator 140 are coupled. For example, when a hook member is formed in the end tool mounting member 130 and the obturator 140, the main body cap 119 may be provided with a fastening hole 119a into which the hook members may be inserted. In an embodiment, a hook member may be formed in the main body cap 119, and a fastening hole may be formed in the end tool mounting member 130 and the obturator 140. In an embodiment, various other coupling members capable of attaching or detaching the main body 110, the end tool mounting member 130, and/or the obturator 140 may be applied.

The cannula 120 may be coupled to one end portion, i.e., a lower end portion of the main body 110, and may have a hollow portion formed therein to allow the surgical instrument 1 to be inserted therethrough. The cannula 120 may be inserted into the body through the patient's navel or skin incision, and in this state, the surgical instrument 1 passing through the main body 110 enters the patient's body through the cannula 120.

Herein, a screw thread 121 may be formed on at least a portion of the outer circumferential surface of the cannula 120. As described above, due to the formation of the screw thread 121 on the outer circumferential surface of the cannula 120, the trocar 100 may be easily inserted into the patient's body while the cannula 120 is rotated. In addition, due to the fixing force of the screw thread 121, even when the cannula 120 is completely inserted and then, the surgical instrument 1 may be allowed to enter along a thin abdominal wall, or even when a tool is removed from the abdominal wall, the cannula 120 may not be separated.

The cannula 120 may further include a fastening portion 125 and an O-ring 126. The fastening portion 125 may be located between the cannula 120 and the main body 110 to connect the cannula 120 with the main body 110. That is, after the fastening portion 125 is fixedly coupled to the cannula 120, the fastening portion 125 may be detachably attached to the main body case 111 of the main body 110. In this case, the fastening portion 125 may include a plurality of hook shapes.

For example, when the hook portion of the fastening portion 125 is pressed, the fastening portion 125 may be elastically deformed and may be inserted into the fastening groove (not shown) of the main body case 111, and in this state, when the pressing of the fastening portion 125 is stopped, the fastening portion 125 may return to an original state, maintaining the binding state with the main body case 111. In some embodiments, various other fastening structures capable of attaching and detaching the cannula 120 to or from the main body 110 may be applied.

Meanwhile, the O-ring 126 may seal in between the main body 110 and the cannula 120.

In the drawings, the cannula 120 and the fastening portion 125 are formed as separate members and are coupled to each other, but the present disclosure is not limited thereto, and the cannula 120 and the fastening portion 125 may be integrally formed as one body.

The end tool mounting member 130 may be detachably formed with respect to the main body 110, and may have an inclined portion 132 formed on an inner circumferential surface thereof so that the end tool 12 of the surgical instrument 1 may be mounted thereon.

Here, the end tool mounting member 130 may overall be cone-shaped or funnel-shaped. In particular, in the present embodiment, the end tool mounting member 130 may be in an asymmetric conical shape (an asymmetric funnel shape) in which distances $d1$, $d2$, $d3$, and $d4$ from the center $C1$ of the conical shape located on the central axis C of the end tool mounting member 130 to points of the edge of the end tool mounting member 130 are different from each other. That is, with respect to the point corresponding to the shortest distance $d1$ from the center $C1$ of the conical shape to the edge of the end tool mounting member 130, the distance from the center $C1$ to the edge of the end tool mounting member 130 is gradually increased in any one direction, and then after the point corresponding to the longest distance $d4$, the distance is gradually decreased again.

In other words, in the present embodiment, the inclined portion 132 is not formed to have the same length as a whole, and may be formed in leaf-like shape in which one area is formed to be longer than the other area. In an embodiment, in other words, the inclined portion 132 may protrude from a funnel main body 131 in one direction, and areas thereof may have different protruding degrees.

However, the concept of the present disclosure is not limited thereto, and the end tool mounting member 130 and the inclined portion 132 formed on the inner circumferential surface thereof may be formed in various sizes and shapes in which the end tool 12 may be mounted.

In this case, the length of the longest portion of the inclined portion 132 of the end tool mounting member 130, that is, the length from the center of the conical shape of the end tool mounting member 130 to the farthest point may be equal to or greater than the length of the end tool 12.

Meanwhile, although the drawings show that the funnel main body 131 and the inclined portion 132 are integrally formed as one body, the present disclosure is not limited thereto, and the funnel main body 131 and the inclined portion 132 may be formed as separate members and then, coupled to each other. In this case, the funnel main body 131 and the inclined portion 132 may be formed to be rotatable with respect to each other.

The obturator 140 may include a head 141 and a blade 142. Here, the obturator 140 may be detachably formed with respect to the main body 110, and may guide the trocar 100 to be inserted into the body of the patient.

The head 141 may be formed in a substantially disk or cylindrical shape, and may seal an upper end portion of the main body 110 while the obturator 140 is coupled to the main body 110.

Here, the head 141 may serve as, for example, a grip portion that is easily held by a user with his or her hand. Accordingly, while holding the head 141 with his or her hand, the user may insert the obturator 140 into the main body 110 or may take the obturator 140 from the main body 110.

The blade 142 may be formed in a thin, long cylindrical shape, and may have one end portion coupled to the head 141 and the other end portion formed in a sharp and pointed shape like a pencil lead. In addition, the blade 142 may be formed to be longer than the cannula 120 by a certain length, and thus, the blade 142 may protrude farther than the cannula 120 by a certain length while the obturator 140 is coupled to the main body 110. Accordingly, the obturator 140 may guide the trocar 100 to be inserted into the body of the patient.

The blade 142 may include a transparent material. Although not shown in the drawings, a certain hole may be formed in an upper portion of the head 141 so that an endoscope camera (not shown) may be inserted therethrough. Accordingly, the trocar 100 may be inserted into the patient's body while the endoscope camera (not shown) is inserted into the blade 142 through the hole, and the process in which the trocar 100 is inserted to an appropriate depth, may be performed while monitoring through the endoscope camera (not shown).

Here, the head 141 and the blade 142 may be integrally formed as one body, or may be formed as separate members and coupled to each other.

When inserted into the patient's body, the trocar 100 is used in a state in which the main body 110, the cannula 120, and the obturator 140 are coupled to one another. That is, while the blade 142 of the obturator 140 leads the path, the trocar 100 may be inserted into the patient's body.

When the trocar 100 is completely inserted, the obturator 140 may be separated from the main body 110. Then, if necessary, the end tool mounting member 130 may be coupled to a position where the obturator 140 has been located.

An aspect of the usage of the trocar 100 according to an embodiment of the present disclosure is as follows.

As described above, when inserted into the patient's body, the trocar 100 is used in a state in which the main body 110, the cannula 120, and the obturator 140 are coupled to one another. That is, while the blade 142 of the obturator 140 leads the insertion path, the trocar 100 may be inserted into the patient's body. Therefore, when the product is released, the main body 110, the cannula 120, and the obturator 140 may be released while being coupled to one another.

When the trocar 100 is completely inserted, the obturator 140 may be separated from the main body 110. Then, the end tool mounting member 130 may be coupled to a position where the obturator 140 has been located.

Next, the surgical instrument 1 may be inserted into the body of the patient through the trocar 100 by using the end tool mounting member 130.

In detail, when the surgical instrument 1, which is used for the multi-joint multi-degree of freedom for laparoscopic surgery, is held with one hand, the end tool 12 is approximately perpendicular to the shaft 14 by its own weight as shown in FIG. 6. In this state, however, since the surgical instrument 1 may not be inserted into the trocar 100, an assistant needs to hold the surgical instrument 1 and adjust the end tool 12 to be parallel with the shaft 14.

In order to solve this problem, the trocar 100 according to an embodiment of the present disclosure includes the end tool mounting member 130, and due to the inclusion of a structure on which the end tool 12 of the surgical instrument 1 is placed thereover, the end tool 12 and the shaft 14 may be easily parallel to each other by the operator, and thus, the insertion thereof into the trocar 100 may be easily made.

Figure 7:
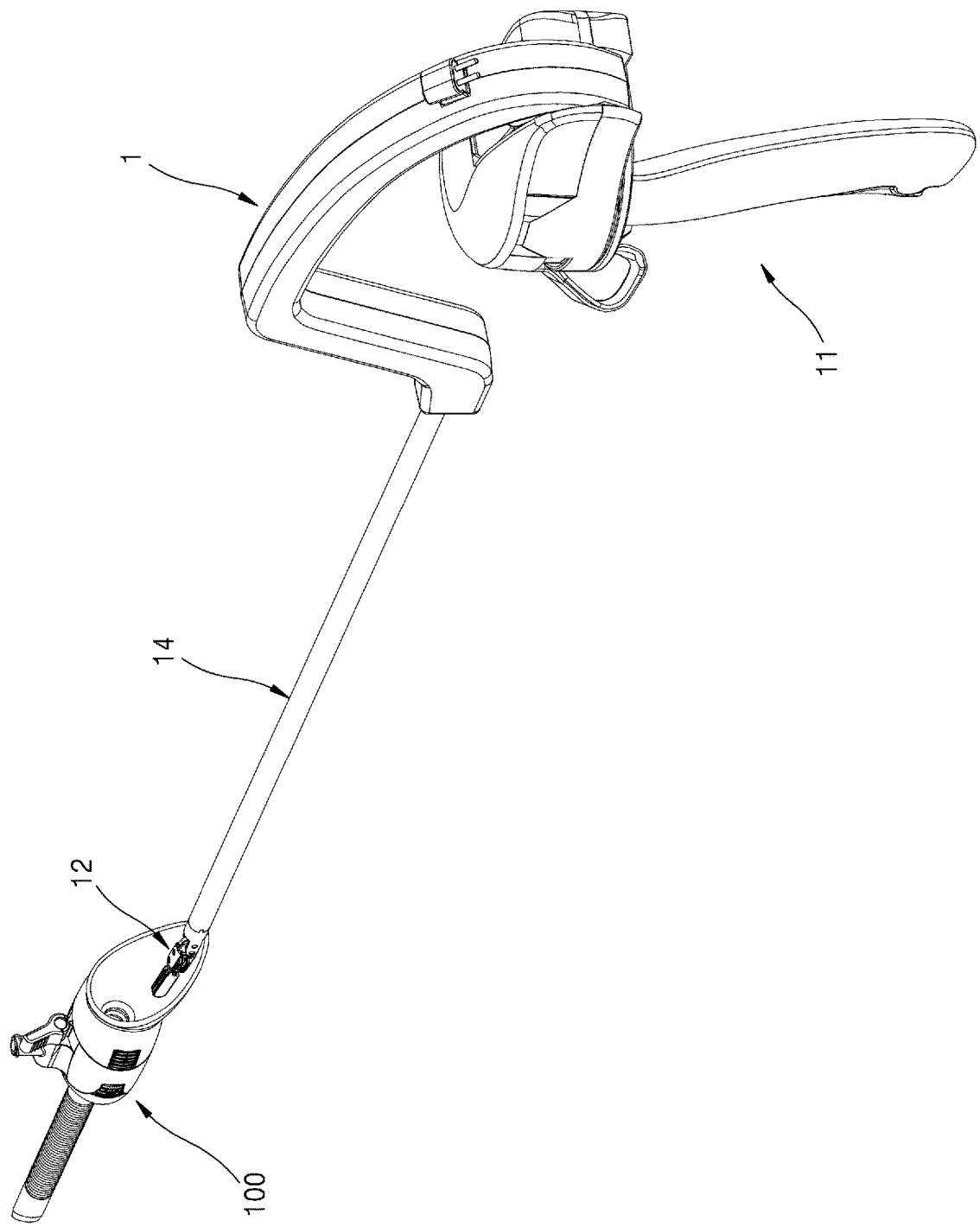

That is, when a control portion 13 of the surgical instrument 1 is rotated in the direction of arrow A illustrated in FIG. 6 in a state where the end tool 12 is placed over the end tool mounting member 130, the end tool 12 is rotated in the direction of arrow B by using the contact point between the end tool 12 and the end tool mounting member 130 as a pivot point, such that the end tool 12 and the shaft 14 are approximately parallel to each other as shown in FIG. 7, and in this state, the surgical instrument 1 is inserted into the main body 110 of the trocar 100.

As described above, since the trocar 100 according to the embodiment of the present disclosure includes the end tool mounting member 130 that can be placed over the end tool 12 of the surgical instrument 1, the end tool 12 and the shaft 14 can be easily parallel to each other by the operator, thereby facilitating the insertion of the end tool 12 into the trocar 100.

MODE OF DISCLOSURE

Figure 8:
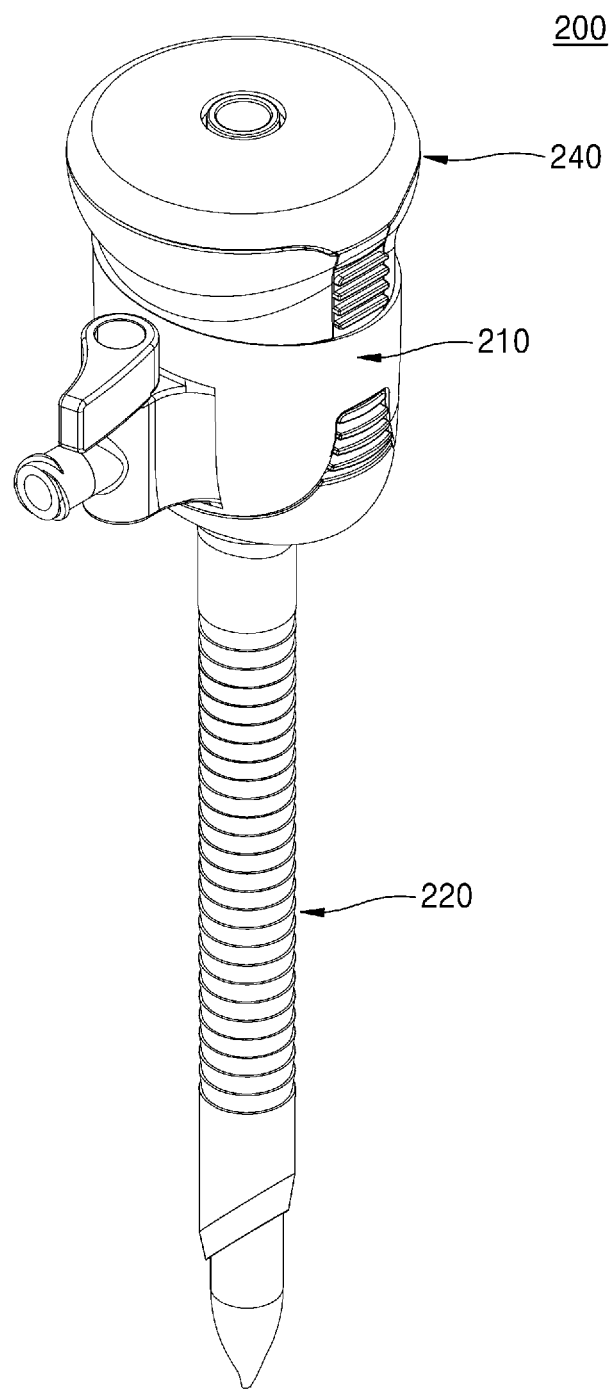
FIG. 8 shows an assembled perspective view illustrating a trocar according to another embodiment of the present disclosure.
Figure 9:
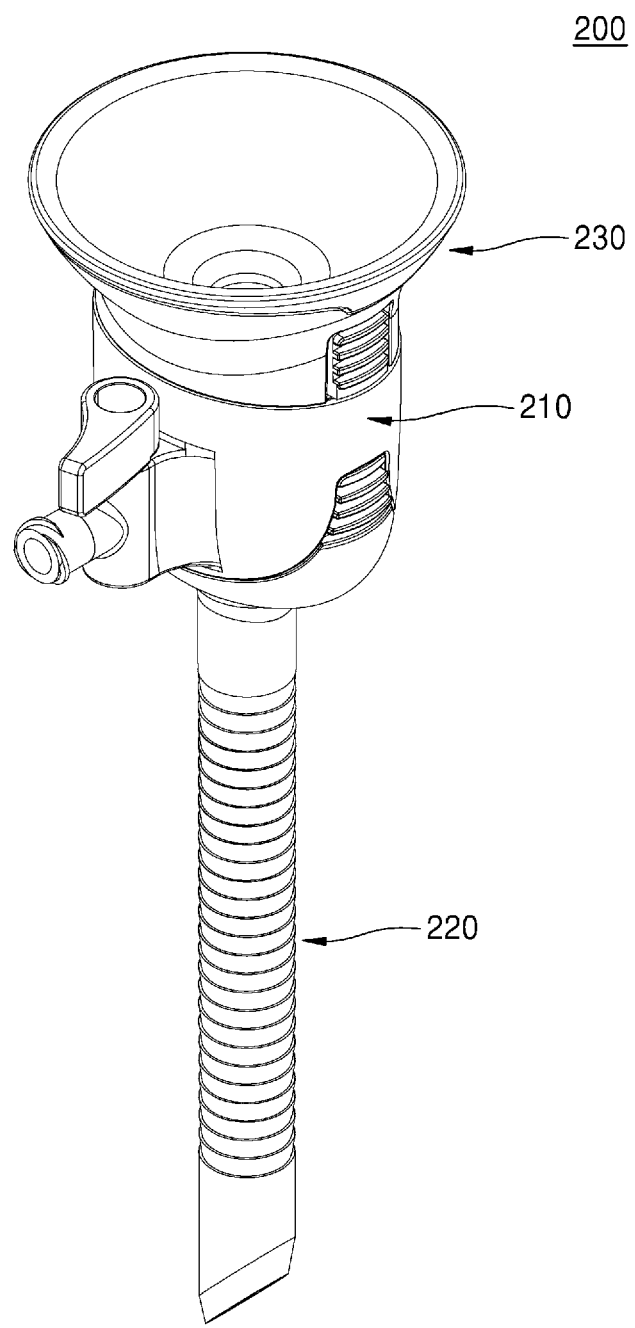
FIG. 9 shows a perspective view illustrating an example of the trocar of FIG. 8 with an obturator coupled thereto instead of an end tool mounting member.

FIG. 8 shows an assembled perspective view illustrating a trocar 200 according to another embodiment of the present disclosure, and FIG. 9 shows a perspective view illustrating an example of the trocar 200 of FIG. 8 with an obturator 240 coupled thereto instead of an end tool mounting member.

Referring to FIGS. 8 to 9, the trocar 200 according to another embodiment of the present disclosure includes a main body 210, a cannula 220, an end tool mounting member 230, and an obturator 240.

The trocar 200 according to the present embodiment of the present disclosure is different from the embodiment in connection with FIG. 1, in that the end tool mounting member 230 is formed in a symmetrical conical shape. That is, the end tool mounting member 230 is formed in a symmetrical conical shape in which the distances from the center of the conical shape to points of the edge of the conical shape are the same. The other parts are substantially the same as or similar to the embodiment shown in FIG. 1, and thus a detailed description thereof will be omitted.

As described above, the present disclosure has been described with reference to the embodiment illustrated in the drawings, but the embodiments are an example only, and those skilled in the art would understand that various modifications can be made on the embodiments. Therefore, the real technical protection range of the present disclosure should be determined by the technical concept of the appended claims.

INDUSTRIAL APPLICABILITY

The present disclosure relates to a trocar, wherein an end tool mounting member is provided to place an end tool of a surgical instrument thereon, thereby facilitating the insertion of the surgical instrument having multiple joints into the trocar.

The invention claimed is:
1. A surgical method using a surgical instrument including an end tool having one or more joints and a trocar, the surgical method comprising:
   coupling an obturator with a main body of the trocar;
   inserting the trocar into a body of a patient;
   separating the obturator from the main body;
   coupling an end tool mounting member with the main body; and
   inserting the surgical instrument into the body of the patient through the trocar,
   wherein in the inserting of the surgical instrument into the body of the patient through the trocar, in a state in which the end tool of the surgical instrument is mounted on the end tool mounting member, when a control portion of the surgical instrument is rotated in a direction, the end tool is rotated in the direction by using a contact point between the end tool and the end tool mounting member as a pivot point, the end tool and a shaft of the surgical instrument are substantially parallel to each other, and then, the surgical instrument is inserted into the body of the patient.

2. The surgical method of claim 1, wherein one of the end tool mounting member and the obturator is selectively coupled to the main body.

3. The surgical method of claim 1, wherein the end tool mounting member is formed to have a conical shape, wherein the end tool mounting member is formed in an asymmetric conical shape in which distances from a center of the conical shape of the end tool mounting member to points of an edge of the conical shape of the end tool mounting member are different from each other.

4. The surgical method of claim 3, wherein with respect to a point corresponding to a shortest distance from among the distances from the center of the conical shape to the edge of the end tool mounting member, a distance from the center of the conical shape to the edge of the end tool mounting member is gradually increased in one direction, and then after a point corresponding to a longest distance, the distance is gradually decreased again.

5. The surgical method of claim 1, wherein the end tool mounting member has an inclined portion formed on an inner circumferential surface thereof so that the end tool of the surgical instrument is mounted thereon.

6. The surgical method of claim 5, wherein the inclined portion protrudes from a funnel main body of the end tool mounting member in one direction, and has areas of which protruding degrees are different from each other.

7. The surgical method of claim 5, wherein a longest length of the inclined portion of the end tool mounting member is equal to or greater than a length of the end tool.

8. The surgical method of claim 1, wherein the obturator is replaced by the end tool mounting member, after the trocar is inserted into the body of the patient in a state in which the obturator is coupled to the main body.

9. The surgical method of claim 1, wherein the end tool is configured to rotate towards a direction of gravity from the shaft of the surgical instrument by a weight of the end tool.

10. The surgical method of claim 1, wherein the main body is configured to be detachably attached to both of the end tool mounting member and the obturator, but the main body accommodates only one of the end tool mounting member and the obturator at a time.

11. The surgical method of claim 1, wherein the trocar comprises a cannula detachably coupled to an end of the main body, and having a hollow portion formed therein to allow the surgical instrument to be inserted therethrough.

12. The surgical method of claim 11, wherein the obturator has a blade and a head, and the blade is longer than the cannula and is comprised of a transparent material.

13. The surgical method of claim 12, wherein the blade and the head are detachably coupled to each other.

14. The surgical method of claim 11, wherein the cannula includes a fastening portion, and the fastening portion is configured to be detachably attached to the main body, includes a plurality of hook shapes, and is comprised of an elastic material, and wherein the fastening portion is detachably attached to the cannula.

* * * * *